(12) United States Patent
Dahmen et al.

(10) Patent No.: US 7,985,178 B2
(45) Date of Patent: Jul. 26, 2011

(54) ENDOSCOPE AND METHOD FOR ITS MANUFACTURING

(75) Inventors: Jan Dahmen, Seitingen-Oberflacht (DE); Frank Fürst, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 978 days.

(21) Appl. No.: 11/550,707

(22) Filed: Oct. 18, 2006

(65) Prior Publication Data

US 2007/0088200 A1 Apr. 19, 2007

(30) Foreign Application Priority Data

Oct. 18, 2005 (DE) .......... 10 2005 051 207

(51) Int. Cl.
*A61B 1/06* (2006.01)
(52) U.S. Cl. ........ 600/182; 600/130; 600/133; 600/138; 600/920
(58) Field of Classification Search .......... 600/182, 600/920
See application file for complete search history.

(56) References Cited

U.S. PATENT DOCUMENTS

| 3,556,086 A * | 1/1971 | Gordon ................ 600/248 |
| 5,290,279 A | 3/1994 | Bonati et al. .............. 606/15 |
| 5,299,560 A | 4/1994 | Hatori ..................... 128/4 |
| 5,429,617 A | 7/1995 | Hammersmark et al. .... 604/264 |
| 2006/0036132 A1* | 2/2006 | Renner et al. .......... 600/160 |
| 2007/0092188 A1 | 4/2007 | Hoefig |

FOREIGN PATENT DOCUMENTS

| DE | 103 07 903 A1 | 9/2004 |
| DE | 10 2004 008458 | 9/2005 |
| EP | 0 025 969 | 4/1981 |
| EP | 0136365 A1 | 4/1985 |
| WO | WO 2004073507 A1 * | 9/2004 |

OTHER PUBLICATIONS

European Search Report, Aug. 1, 2007, 7 pages.

* cited by examiner

*Primary Examiner* — Matthew J Kasztejna
(74) *Attorney, Agent, or Firm* — St. Onge Steward Johnston & Reens LLC

(57) ABSTRACT

An endoscope has a shaft which is composed of an outer tube and an inner tube, providing a channel therebetween. The proximal end of the shaft is connected to an endoscope head. The endoscope head is provided with a light guide connector. Light guides extend from said light guide connector to a distal end of said channel in said shaft. Said channel housing said light guides is filled with an adhesive.

1 Claim, 4 Drawing Sheets

ENDOSCOPE AND METHOD FOR ITS MANUFACTURING

BACKGROUND OF THE INVENTION

The invention relates to an endoscope, the shaft of which comprises an outer tube and an inner tube inserted into said outer tube. A channel is disposed between the outer side of said inner tube and the inner side of said inner tube. An endoscope head houses a proximal end of the shaft. A light connector projects, in particular laterally, from said endoscope head. Light guides extend from said light guide connector to a distal end of said channel for guiding light from said light connector to the distal end of the endoscope for illuminating purposes.

Endoscopes of this type are generally known.

Endoscopes are generally used in so-called minimal-invasive surgeries, for example arthroscopy, gastrointestinal examinations and chest cavity examinations, in case of ruptures and during joint and spinal column surgeries.

Within the inner tube, a so-called optic is accommodated, generally a rod lens system or an electronic image recording and conversion system.

In order to illuminate the operation side with light, a light guide system is arranged within the endoscope. The light guide system which usually is composed of a bundle of light guiding fibers, in particular glass fibers, is usually housed loosely in the channel between the inner and the outer tube. Additionally, the bundle of light fibers is loosely guided to the proximal end of the light guide connector within the endoscope head.

For sealing purposes, the opposite end sections of the light guides are tightly and sealingly fixed at the distal end of the shaft on the one side and on the proximal end of the light guide connector on the other side.

In minimal-invasive surgery, very small incisions with a length of about half an inch are made in the body for inserting the endoscope into the body. For it, the shafts of the endoscopes should be designed as thin as possible.

This results in the shaft not being mechanically very robust, in particular in terms of bending of the shaft.

When the endoscope is being handled, irrespective of whether it is during an intervention or during the subsequent cleaning and autoclaving processes, forces that are applied can result in a bending of the shaft. A bending of the shaft also bends the inner tube containing the optic system, which can lead to fracture and/or some detachments, for example on the rod lenses of the optics system.

Fracture cracks at the distal and proximal sealing points of the light guides can result in moisture entering into the channel housing the light guides. This moisture can contain aggressive cleaning liquids, for example peroxide containing liquids, which leads to the destruction of the very fine glass fibers during autoclaving. Additionally, the loose fibers can break when the shaft is bent remarkably.

As a result, the lifetime of the endoscope is shortened.

It is, therefore, an object of the present invention to provide an endoscope with an extended lifetime.

It is a further object of the present invention to provide a method for manufacturing an endoscope with an extended lifetime.

SUMMARY OF THE INVENTION

The object is achieved by an endoscope having a shaft, said shaft comprising an outer tube and an inner tube inserted into said outer tube, a channel being disposed between an outer side of said inner tube and an inner side of said inner tube, an endoscope head housing a proximal end of said shaft, a light guide connector projecting from said endoscope, and light guides extending from said light guide connector to a distal end of said channel, wherein said channel housing said light guides is filled with an adhesive.

Filling the channel containing the light guides leads to a mechanically reinforced shaft. The optical light guides which are passed through the channel are now embedded within the adhesive. The embedding protects the individual fibers of the optical light guide as in a composite material.

A channel which has additionally been filled with an adhesive which is cured is more resistant to bending. This protects the individual optical light guides from breakage.

The individual fibers embedded in the cured adhesive show a long lifetime, resulting in an endoscope which is capable of illuminating the operating side with high light intensity even after frequent use.

The adhesive additionally protects the optical fibers against penetration of moisture and/or chemically aggressive cleaning fluids. The adhesive also seals the entire channel, in particular at its distal and proximal end sections. This prevents moisture from entering during autoclaving cycles into the channel and prevents a damage of the optical light guides during further autoclaving cycles.

The filling of the channel in the area between the inner and the outer tube with the adhesive leads to a rigid outer protection shell for the inner tube housing the optical system, in particular the long rod lenses made of glass. This results in an endoscope shaft being stiffer than an endoscope shaft without the filling adhesive.

In a refinement of the invention, the optical light guides are passed from the proximal end of the endoscope shaft to a lateral extending light guide connector in a cavity within the endoscope head, and this cavity is likewise filled with the adhesive.

This measure has the advantage that both, the channel between the inner and the outer tube of the shaft and the cavity within the endoscope head are filled with the adhesive. This protects the entire internal area in which the optical light guides are housed against the ingress of chemicals or body fluids. Ingress of moisture into the interior of the endoscope is completely prevented in this way. This protects the optical light guides against being damaged during consecutive autoclaving cycles and thus extends remarkably the life of the endoscope.

In a refinement of the invention, at least one opening is provided in the endoscope for introducing the adhesive.

This measure has the advantage that the inner space housing the light guides can be filled with the liquid adhesive via the at least one opening provided in the endoscope. This ensures that no air bubbles remain in the space, since this results in air being forced out of the interior via the distal end or the proximal end of the endoscope during the filling process. Both, the cavity and the channel in the shaft can be filled with adhesive without any remaining air bubbles. In consequence, the optical light guides are completely and permanently sheathed with adhesive and are protected against any moisture.

In a refinement of the invention, the at least one opening is provided in the area of a mouth of the light guide connector.

This measure has the advantage that an area into which one end of the optical light guide opens can be filled with the adhesive. This results in the cavity in the endoscope head being filled with the adhesive first of all and air contained therein being forced out. In this case, the adhesive sheaths an area of the optical light guides located in the cavity. As the filling process continues, the adhesive is forced out of this cavity into the channel in the endoscope shaft. This continues until the adhesive emerges at the distal end of the endoscope shaft, thus ensuring that the endoscope is entirely filled with the adhesive without any remaining air bubbles, with the result, that the optical light guides are completely sheathed and embedded in the adhesive.

As an alternative measure, the filling process can also be carried out from the distal end of the shaft.

In a refinement of the invention, the at least one opening is provided in the outer tube of the shaft.

This measure allows the filling process starting with inserting the adhesive via the opening in the outer tube. Depending on the location where the opening is provided, the liquid adhesive penetrates in both directions, i.e. into the proximal and the distal direction. If there are a plurality of openings, this makes it possible to fill the endoscope with adhesive via the several openings. This is particularly advantageous when using highly viscous adhesives. With regard to the methods of manufacturing the endoscope according to the invention, this method contains the step of filling the channel housing said light guides with a liquid adhesive, followed by curing the adhesive.

An advantage of the method is that the adhesive can be introduced after the optical light guides have already been inserted into the channel. As a result, the openings at the ends of the optical light guide channel can be sealed with the adhesive, too. Therefore, there is no need of using particular sealings like sealing rings or end caps, which are subject to wear, to seal the endoscope.

In a refinement of the method, the adhesive is introduced from one end into the space in which the optical light guides are housed, until it emerges at the other end of the space.

This measure has the advantage that the endoscope can be filled with the adhesive without any remaining bubbles. This leads to a uniform distribution of the adhesive, and to a uniform sheathing of the optical light guides with adhesive. Thus it is possible to produce a composite material with homogeneous characteristics over its entire area.

The adhesive may be a single-component adhesive.

This measure has the advantage that a single ready-to-use adhesive can be used for assembling the endoscope. Once the endoscope is filled with the adhesive, the adhesive is then cured by variation of the ambient conditions. This can be done by raising the temperature. Single-component adhesives usually have the advantage of a longer processing time. This allows corrections to be made to the endoscope during the filling process.

The adhesive can also be a multiple-component adhesive.

This measure has the advantage that the multiple-component adhesive can be mixed shortly before application. As the reaction progresses, the adhesive becomes more and more viscous and firmer and finally solid. The curing time can be determined by the variation of the composition of the components. This saves time for assembling the endoscope.

In a further refinement of the invention, after the adhesive has cured, the endoscope is ground and polished at the distal end of the endoscope shaft and at the mouth of the light guide connector.

This results in plane surfaces at the mouth of the light guide connector on the one side and the distal end of the endoscope shaft on the other side. This allows a light source to be connected to the light guide connector in a manner, that light can be transmitted through the optical light guides uniformly without any loss of stray light. Additionally, the light can be emitted from the distal end of the shaft without stray light.

It is self-evident that the features mentioned above and those still to be explained in the following text can be used not only in the respectively stated combination but also in other combinations or on their own without departing from the scope of the present invention.

BRIEF DESCRIPTION OF THE DRAWINGS

The invention will be described and explained in more detail in the following text with reference to embodiments in connection with the attached drawings, in which.

DETAILED DESCRIPTION OF PREFERRED EMBODIMENTS

Figure 1:
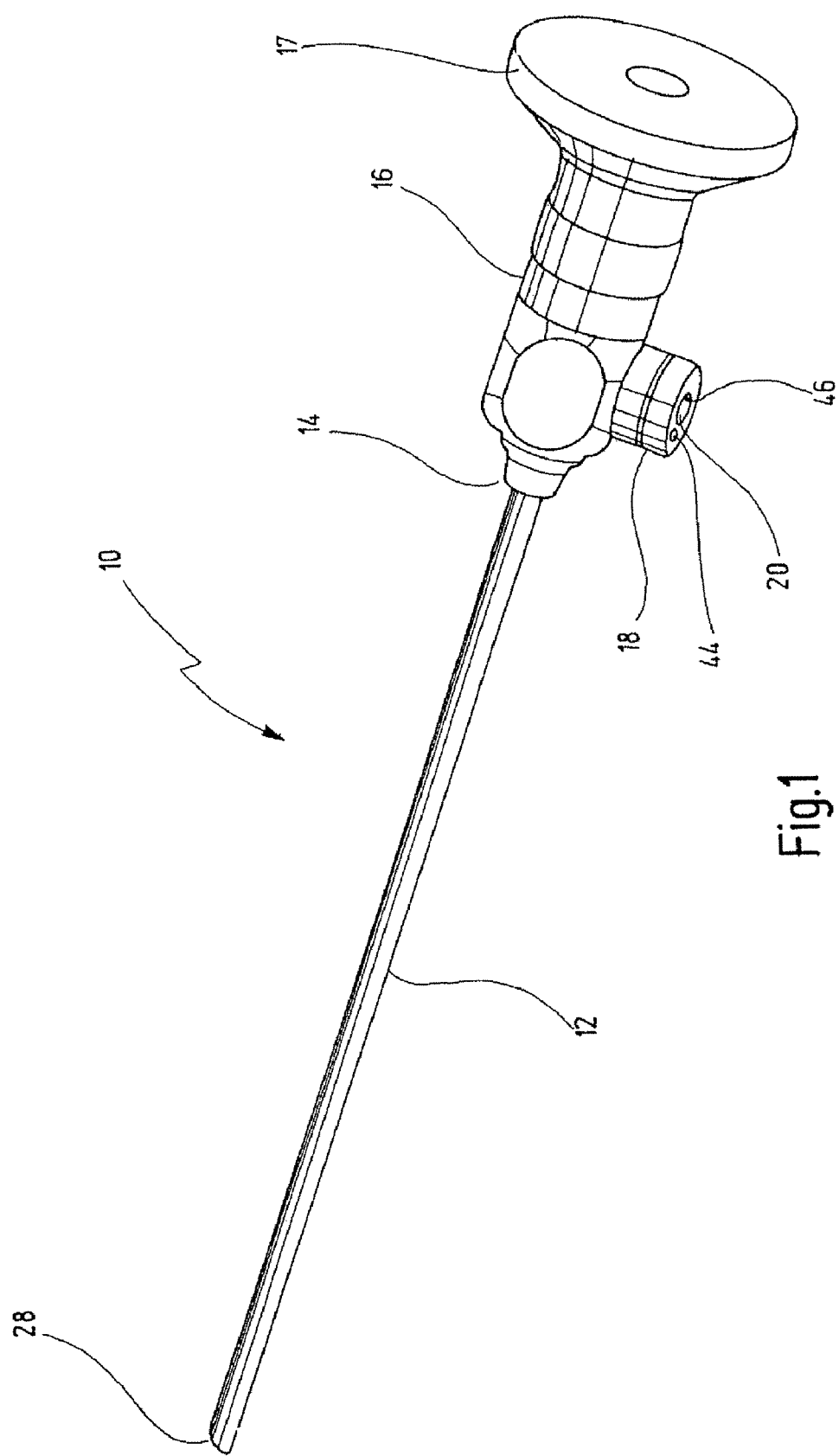
FIG. 1 shows a perspective view of an endoscope according to the invention.

FIG. 1 shows an endoscope which is designed in its totality with the reference number 10.

The endoscope 10 has a shaft 12. The shaft 12 is housed at its proximal end 14 in an endoscope head 16. The endoscope head 16 has a light guide connector 18, projecting laterally from the endoscope head 16. A proximal end of the endoscope head 16 shows an ocular 17.

Figure 2:
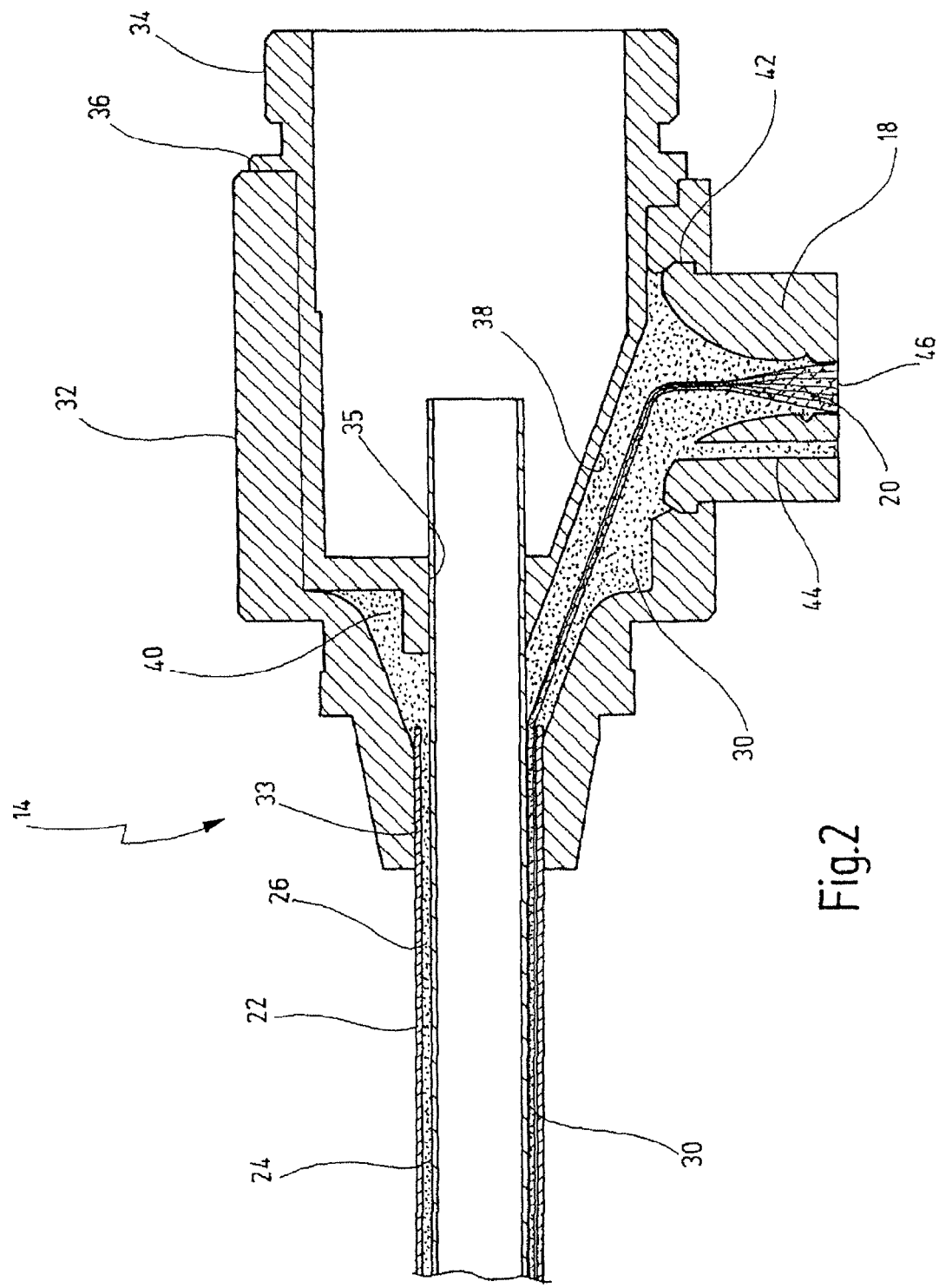
FIG. 2 shows a partly longitudinal section through the endoscope of FIG. 1.

As can be seen from FIG. 2, the endoscope shaft 12 has a first outer tube 22. A second inner tube 24 having a smaller diameter is inserted into the first tube 22. First tube 22 and second tube 24 are arranged coaxially with respect to another. An annular channel 26 is formed in the endoscope shaft 12 between the inner side of the outer shaft 22 and the outer side of the inner tube 24.

The endoscope head 16 has a first outer sleeve 32 and a second inner sleeve 34. The outer sleeve 32 has the light connector 18 projecting laterally from the first sleeve 32. The light guide connector 18 has a fitting 42 which is also designed as a hollow sleeve. The first sleeve 32 tapers towards the shaft 12. The first outer tube 22 of the shaft 12 is held in the taper 33 in such a way that it projects somewhat into the interior of the first sleeve 32.

The second sleeve 34 has an annular flange 36 which rests on a proximal end of the first sleeve 32 in a tight manner. The second inner tube 24 extends into the inner sleeve 34. The second tube 24 is held tightly fixed in a passage 35 of the second sleeve 34.

The second sleeve 34 has an incline 38. This incline 38 tapers, when seen to the distal end, in such a way that a cavity 40 is formed between the first sleeve 32 and the second sleeve 34.

Optical light guides 20 which are a bundle of thin long glass fibers extend from a mouth 46 of the light guide connector 18 through the inner cavity 40 and the channel 26 between inner tube 24 and outer tube 22 up to the distal end 28 of the shaft 12. Both, the channel 26 and the cavity 40 within the endoscope head 16 are filled with an adhesive 30 which is cured. The cured adhesive results in a strong solid mass having embedded the glass fiber bundle.

The hardened adhesive 30 in the channel 26 not only provides an embedding and fixing of the glass fibers within said channel, but also provides a stiffening to the shaft assembly, in particular to the inner tube 24 housing rod lenses of the optical system.

The method for manufacturing the endoscope 10 comprises to pass the optical light guides 20 into the interior of first tube 22 which is sealingly connected to the outer sleeve 32. The optical light guides 20 are fed to the light guide connector 18 and pass beyond the mouth 46 of the fitting 42.

The second tube 24, firmly connected to the second sleeve 34, is inserted into the first tube 22 until the second sleeve 34 comes into contact with the annular flange 36. The optical system, i.e. the rod lenses, may already be inserted into the tube 24 or at a later stage. The ocular 17 can be mounted on an outer mounting flange of the second sleeve 34 for closing the endoscope head 16 proximally.

Figure 3:
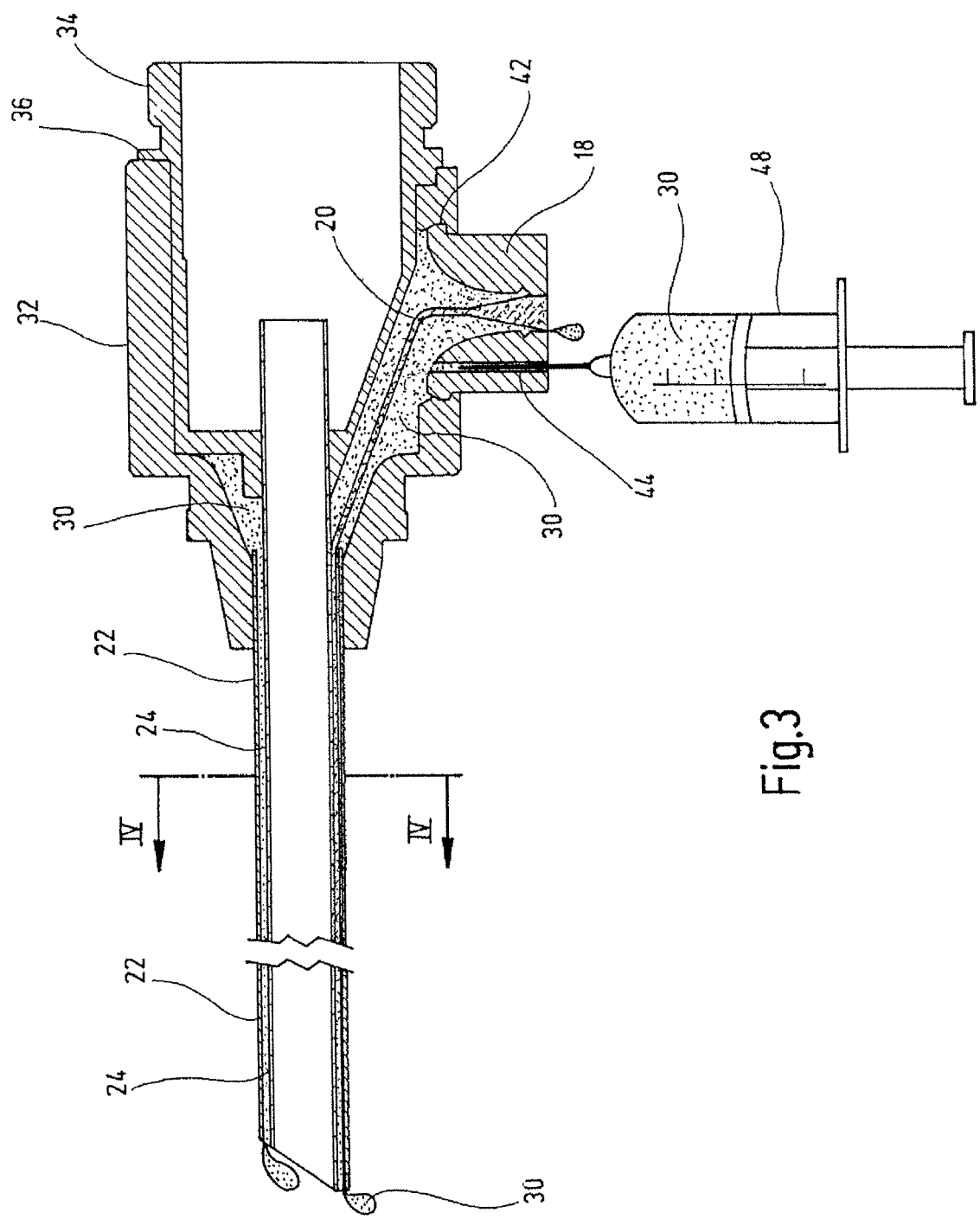
FIG. 3 shows the endoscope of FIGS. 1 and 2, during a method step according to the invention.
Figure 4:
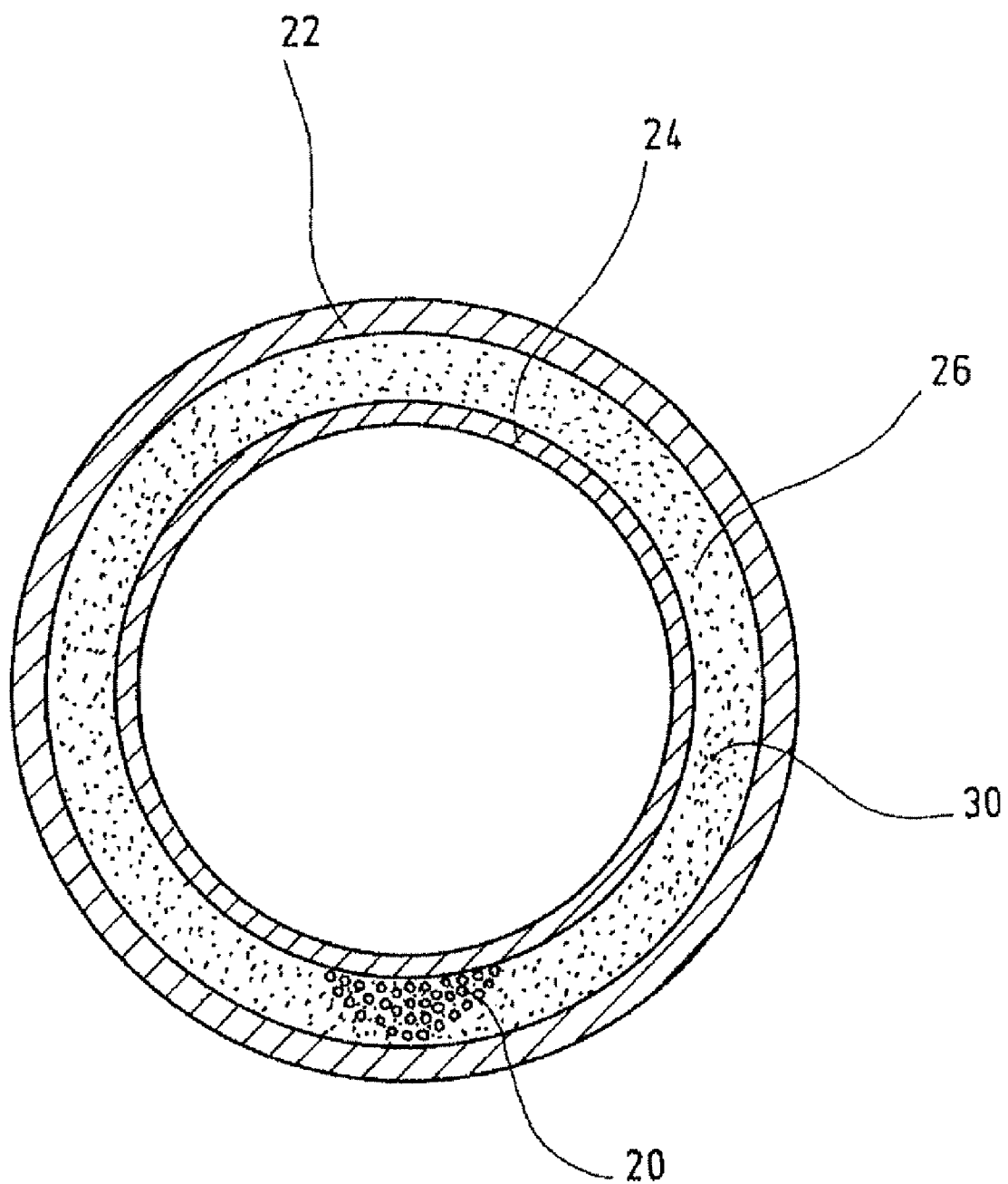
FIG. 4 shows a section along the line IV-IV in FIG. 3.

As can be seen from FIG. 3, a liquid adhesive 30 can be inserted via an opening 44 provided in the fitting 42 via a kind of syringe 48. With this, the cavity 40 in the endoscope head 16 is first filled with the liquid adhesive 30. Air contained within the cavity 40 can be passed out of mouth 46 or pressed into the channel 26. When further introducing the adhesive liquid 30, it penetrates also into the channel 26 between inner tube 24 and outer tube 22. The adhesive 30 is introduced until it passes at the distal end as shown in FIG. 3.

If wanted, the light guides 20 can be widened in the area of the mouth 46 to a kind of cone.

After filling the entire inner space, i.e. the cavity 40 and the channel 26, with adhesive 30, the filling is terminated.

Now, the adhesive 30 is cured. Depending on the nature of the adhesive, it is done by raising the temperature or by starting a polymerization process, for example by sheathing, illuminating or the like.

In a final step, after the adhesive 30 has cured, the distal end 28 of the shaft is ground and polished and the mouth 46 of the light guide connector 18 is ground and polished, too.

It is also possible to provide at least one opening in the outer tube 22 and to insert the liquid adhesive 30 via the opening into the channel 26 between outer tube 22 and inner tube 24. The still liquid adhesive 30 can enter the cavity 40, and, after filling it, the adhesive 30 passes the mouth 46 of light connector. In this case opening 44 can be omitted.

The invention claimed is:

1. An endoscope, having a shaft, said shaft comprising an outer tube, an inner tube inserted into said outer tube, a channel being disposed between an outer side of said inner tube and an inner side of said outer tube, an endoscope head housing a proximal end of said shaft, a light guide connector projecting from said endoscope head and having a terminal mouth opening, and light guides extending from said terminal mouth opening of said light guide connector to a distal end of said shaft, said endoscope head having a cavity, in which said light guides are passed from said proximal end of said shaft to said terminal mouth opening of said light guide connector, wherein said channel housing said light guides and said cavity are both filled completely with a cured adhesive, and wherein said light guide connector comprises a hollow sleeve and said light guides extend through said hollow sleeve, and; wherein a bore is provided in a wall of said hollow sleeve, said bore extending from a level of said terminal mouth opening to said cavity and opening into said cavity for filling said cavity with said adhesive, and said bore being separated from an inner hollow space of said hollow sleeve.

\* \* \* \* \*